(12) United States Patent
Vanhove et al.

(10) Patent No.: US 10,689,444 B2
(45) Date of Patent: *Jun. 23, 2020

(54) RECOMBINANT MONOVALENT ANTIBODIES

(71) Applicants: OSE Immunotherapeutics, Nantes (FR); Institut National de la Sante et de la Recherche Medicale (INSERM), Paris (FR)

(72) Inventors: Bernard Vanhove, Reze (FR); Caroline Mary, Sainte Pazanne (FR); Flora Coulon, Saint Georges de Montaigu (FR)

(73) Assignees: OSE Immunotherapeutics, Nantes (FR); Institut National de la Sante et de la Recherche Medicale, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/416,513

(22) Filed: Jan. 26, 2017

(65) Prior Publication Data

US 2017/0166643 A1    Jun. 15, 2017

Related U.S. Application Data

(63) Continuation of application No. 13/144,471, filed as application No. PCT/IB2010/000196 on Jan. 13, 2010, now Pat. No. 9,587,023.

(30) Foreign Application Priority Data

Jan. 14, 2009 (EP) .................................... 09290029

(51) Int. Cl.
  *C07K 16/28*  (2006.01)
  *A61K 39/00*  (2006.01)

(52) U.S. Cl.
  CPC .... *C07K 16/2818* (2013.01); *A61K 2039/505* (2013.01); *C07K 2317/14* (2013.01); *C07K 2317/35* (2013.01); *C07K 2317/52* (2013.01); *C07K 2317/524* (2013.01); *C07K 2317/526* (2013.01); *C07K 2317/56* (2013.01); *C07K 2317/565* (2013.01); *C07K 2317/74* (2013.01); *C07K 2317/94* (2013.01); *C07K 2318/10* (2013.01); *C07K 2319/00* (2013.01); *Y02A 50/41* (2018.01)

(58) Field of Classification Search
None
See application file for complete search history.

(56) References Cited

U.S. PATENT DOCUMENTS

| | | | |
|---|---|---|---|
| 7,408,041 B2 | 8/2008 | Bowdish et al. | |
| 8,785,604 B2 * | 7/2014 | Mary ................. | C07K 16/2818 424/144.1 |
| 9,562,098 B2 * | 2/2017 | Mary ................. | C07K 16/2818 |
| 9,587,023 B2 * | 3/2017 | Vanhove ............ | C07K 16/2818 |
| 2004/0033561 A1 | 2/2004 | O'Keefe et al. | |
| 2006/0062784 A1 * | 3/2006 | Grant ................. | C07K 16/2875 424/141.1 |
| 2006/0094062 A1 | 5/2006 | Wu et al. | |
| 2007/0071675 A1 | 3/2007 | Wu et al. | |
| 2008/0038273 A1 | 2/2008 | Soulillou et al. | |
| 2010/0255012 A1 | 10/2010 | Schuurman et al. | |
| 2011/0097339 A1 | 4/2011 | Holmes et al. | |

FOREIGN PATENT DOCUMENTS

| | | |
|---|---|---|
| WO | 02/051871 A2 | 7/2002 |
| WO | 2004/058820 A2 | 7/2004 |
| WO | 2005/063816 A2 | 7/2005 |
| WO | 2007/048037 A2 | 4/2007 |
| WO | 2007/087673 A1 | 8/2007 |
| WO | 2008/145138 A1 | 12/2008 |

OTHER PUBLICATIONS

Webber et al., "Preparation and Characterization of a Disulfide-Stabilized Fv Fragment of the Anti-Tac Antibody: Comparison with its Single-Chain Analog," Molecular Immunology, 32: 249-258 (1995).
Jain et al., "Engineering antibodies for clinical applications," Trends in Biotechnology, 25: 307-316 (2007).
Paul ed., "Fundamental Immunology: Immunogenicity and Antigen Structure," 242 (1993).
Labrijn et al., "When binding is enough: nonactivating antibody formats," Current Opinion in Immunology, 20: 479-485 (2008).

* cited by examiner

*Primary Examiner* — Brad Duffy
(74) *Attorney, Agent, or Firm* — Morgan, Lewis & Bockius LLP

(57) ABSTRACT

The invention relates to recombinant monovalent antibodies which are heterodimers of a first protein chain comprising the variable domain of the heavy chain of an antibody of interest and the CH2 and CH3 domains of an IgG immunoglobulin and a second protein chain comprising the variable domain of the light chain of said immunoglobulin of interest and the CH2 and CH3 domains of said IgG immunoglobulin. These antibodies can be used in particular as therapeutic agents in all cases where monovalent binding to a ligand such a cellular receptor is required.

11 Claims, 10 Drawing Sheets

Figure 1C:
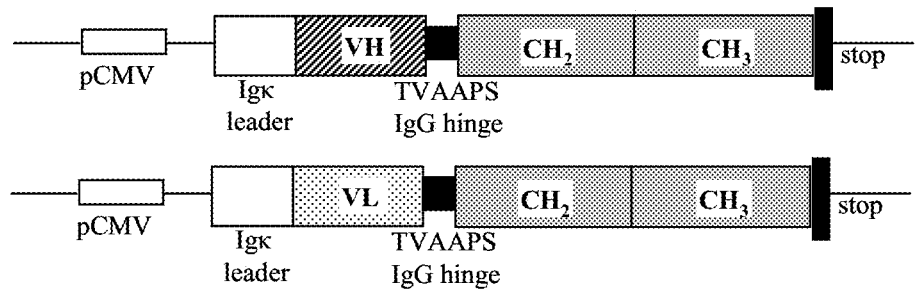

Specification includes a Sequence Listing.

| | | |
|---|---|---|
| 1 | GTC AAG CTG CAG CAG TCA GGA GCT GAG CTG GTG AAA CCC GGG GCG | 45 |
| 1 | Val Lys Leu Gln Gln Ser Gly Ala Glu Leu Val Lys Pro Gly Ala | 15 |
| 46 | TCG GTG AGG CTG TCC TGC AAG GCG TCT GGT TAC ACC TTC ACT GAA | 90 |
| 16 | Ser Val Arg Leu Ser Cys Lys Ala Ser Gly Tyr Thr Phe Thr Glu | 30 |
| 91 | TAT ATT ATA CAC TGG ATA AAG CTG AGG TCT GGA CAG GGT CTT GAG | 135 |
| 31 | Tyr Ile Ile His Trp Ile Lys Leu Arg Ser Gly Gln Gly Leu Glu | 45 |
| 136 | TGG ATT GGG TGG TTT TAC CCT GGA AGT AAT GAT ATA CAG TAC AAT | 180 |
| 46 | Trp Ile Gly Trp Phe Tyr Pro Gly Ser Asn Asp Ile Gln Tyr Asn | 60 |
| 181 | GCG AAA TTC AAG GGC AAG GCC ACA TTG ACT GCG GAC AAA TCC TCC | 225 |
| 61 | Ala Lys Phe Lys Gly Lys Ala Thr Leu Thr Ala Asp Lys Ser Ser | 75 |
| 226 | AGC ACC GTC TAT ATG GAA CTT ACT GGA TTG ACA TCT GAG GAC TCT | 270 |
| 76 | Ser Thr Val Tyr Met Glu Leu Thr Gly Leu Thr Ser Glu Asp Ser | 90 |
| 271 | GCG GTC TAT TTC TGT GCA AGA CGC GAC GAT TTC TCT GGT TAC GAC | 315 |
| 91 | Ala Val Tyr Phe Cys Ala Arg Arg Asp Asp Phe Ser Gly Tyr Asp | 105 |
| 316 | GCC CTT CCT TAC TGG GGC CAA GGG ACC ATG GTC ACC GTC TCC TCA | 360 |
| 106 | Ala Leu Pro Tyr Trp Gly Gln Gly Thr Met Val Thr Val Ser Ser | 120 |
| 361 | act gtg gct gca cca tct GCT CCA GCA CCT GAA CTC CTG GGG GGA | 405 |
| 121 | Thr Val Ala Ala Pro Ser Ala Pro Ala Pro Glu Leu Leu Gly Gly | 135 |
| 406 | CCG TCA GTC TTC CTC TTC CCC CCA AAA CCC AAG GAC ACC CTC ATG | 450 |
| 136 | Pro Ser Val Phe Leu Phe Pro Pro Lys Pro Lys Asp Thr Leu Met | 150 |
| 451 | ATC TCC CGG ACC CCT GAG GTC ACA TGC GTG GTG GTG GAC GTG AGC | 495 |
| 151 | Ile Ser Arg Thr Pro Glu Val Thr Cys Val Val Val Asp Val Ser | 165 |
| 496 | CAC GAA GAC CCT GAG GTC AAG TTC AAC TGG TAC GTG GAC GGC GTG | 540 |
| 166 | His Glu Asp Pro Glu Val Lys Phe Asn Trp Tyr Val Asp Gly Val | 180 |
| 541 | GAG GTG CAT AAT GCC AAG ACA AAG CCG CGG GAG GAG CAG TAC AAC | 585 |
| 181 | Glu Val His Asn Ala Lys Thr Lys Pro Arg Glu Glu Gln Tyr Asn | 195 |
| 586 | AGC ACG TAC CGT GTG GTC AGC GTC CTC ACC GTC CTG CAC CAG GAC | 630 |
| 196 | Ser Thr Tyr Arg Val Val Ser Val Leu Thr Val Leu His Gln Asp | 210 |
| 631 | TGG CTG AAT GGC AAG GAG TAC AAG TGC AAG GTC TCC AAC AAA GCC | 675 |
| 211 | Trp Leu Asn Gly Lys Glu Tyr Lys Cys Lys Val Ser Asn Lys Ala | 225 |
| 676 | CTC CCA GCC CCC ATC GAG AAA ACC ATC TCC AAA GCC AAA GGG CAG | 720 |
| 226 | Leu Pro Ala Pro Ile Glu Lys Thr Ile Ser Lys Ala Lys Gly Gln | 240 |
| 721 | CCC CGA GAA CCA CAG GTG TAC ACC CTG CCC CCA TCC CGG GAG GAG | 765 |
| 241 | Pro Arg Glu Pro Gln Val Tyr Thr Leu Pro Pro Ser Arg Glu Glu | 255 |
| 766 | ATG ACC AAG AAC CAG GTC AGC CTG ACC TGC CTG GTC AAA GGC TTC | 810 |
| 256 | Met Thr Lys Asn Gln Val Ser Leu Thr Cys Leu Val Lys Gly Phe | 270 |
| 811 | TAT CCC AGC GAC ATC GCC GTG GAG TGG GAG AGC AAT GGG CAG CCG | 855 |
| 271 | Tyr Pro Ser Asp Ile Ala Val Glu Trp Glu Ser Asn Gly Gln Pro | 285 |

Figure 1A

```
856   GAG AAC AAC TAC AAG ACC ACG CCT CCC GTG CTG GAC TCC GAC GGC   900
286   Glu Asn Asn Tyr Lys Thr Thr Pro Pro Val Leu Asp Ser Asp Gly   300

901   CCC TTC TTC CTC TAT AGC AAG CTC ACC GTG GAC AAG AGC AGG TGG   945
301   Pro Phe Phe Leu Tyr Ser Lys Leu Thr Val Asp Lys Ser Arg Trp   315

946   CAG CAG GGG AAC GTC TTC TCA TGC TCC GTG ATG CAT GAG GCT CTG   990
316   Gln Gln Gly Asn Val Phe Ser Cys Ser Val Met His Glu Ala Leu   330

991   CAC AAC CAC TAC ACG CAG AAG AGC CTC TCC CTG TCT CCG GGT AAA   1035
331   His Asn His Tyr Thr Gln Lys Ser Leu Ser Leu Ser Pro Gly Lys   345

1036  TAA   1038
346   End
```

Figure 1A (continued)

```
  1    GAC ATC CAG ATG ACC CAG TCT CCA GCC TCC CTA TCT GTT TCT GTG    45
  1    Asp Ile Gln Met Thr Gln Ser Pro Ala Ser Leu Ser Val Ser Val    15

46    GGA GAA ACT GTC ACC ATC ACG TGT CGA ACA AAT GAA AAT ATT TAC    90
 16    Gly Glu Thr Val Thr Ile Thr Cys Arg Thr Asn Glu Asn Ile Tyr    30

91    AGT AAT TTA GCA TGG TAT CAG CAG AAA CAG GGA AAA TCT CCT CAG   135
 31    Ser Asn Leu Ala Trp Tyr Gln Gln Lys Gln Gly Lys Ser Pro Gln    45

136    CTC CTG ATC TAT GCT GCA ACA CAC TTA GTA GAG GGT GTG CCA TCA   180
 46    Leu Leu Ile Tyr Ala Ala Thr His Leu Val Glu Gly Val Pro Ser    60

181    AGG TTC AGT GGC AGT GGA TCA GGC ACA CAG TAT TCC CTC AAG ATC   225
 61    Arg Phe Ser Gly Ser Gly Ser Gly Thr Gln Tyr Ser Leu Lys Ile    75

226    ACC AGC CTG CAG TCT GAA GAT TTT GGG AAT TAT TAC TGT CAA CAC   270
 76    Thr Ser Leu Gln Ser Glu Asp Phe Gly Asn Tyr Tyr Cys Gln His    90

271    TTT TGG GGT ACT CCG TGC ACG TTC GGA GGG GGG ACC AAG CTG GAA   315
 91    Phe Trp Gly Thr Pro Cys Thr Phe Gly Gly Gly Thr Lys Leu Glu   105

316    ATA AAA CGG act gtg gct gca cca tct GCT CCA GCA CCT GAA CTC   360
106    Ile Lys Arg Thr Val Ala Ala Pro Ser Ala Pro Ala Pro Glu Leu   120

361    CTG GGG GGA CCG TCA GTC TTC CTC TTC CCC CCA AAA CCC AAG GAC   405
121    Leu Gly Gly Pro Ser Val Phe Leu Phe Pro Pro Lys Pro Lys Asp   135

406    ACC CTC ATG ATC TCC CGG ACC CCT GAG GTC ACA TGC GTG GTG GTG   450
136    Thr Leu Met Ile Ser Arg Thr Pro Glu Val Thr Cys Val Val Val   150

451    GAC GTG AGC CAC GAA GAC CCT GAG GTC AAG TTC AAC TGG TAC GTG   495
151    Asp Val Ser His Glu Asp Pro Glu Val Lys Phe Asn Trp Tyr Val   165

496    GAC GGC GTG GAG GTG CAT AAT GCC AAG ACA AAG CCG CGG GAG GAG   540
166    Asp Gly Val Glu Val His Asn Ala Lys Thr Lys Pro Arg Glu Glu   180

541    CAG TAC AAC AGC ACG TAC CGT GTG GTC AGC GTC CTC ACC GTC CTG   585
181    Gln Tyr Asn Ser Thr Tyr Arg Val Val Ser Val Leu Thr Val Leu   195

586    CAC CAG GAC TGG CTG AAT GGC AAG GAG TAC AAG TGC AAG GTC TCC   630
196    His Gln Asp Trp Leu Asn Gly Lys Glu Tyr Lys Cys Lys Val Ser   210

631    AAC AAA GCC CTC CCA GCC CCC ATC GAG AAA ACC ATC TCC AAA GCC   675
211    Asn Lys Ala Leu Pro Ala Pro Ile Glu Lys Thr Ile Ser Lys Ala   225

676    AAA GGG CAG CCC CGA GAA CCA CAG GTG TAC ACC CTG CCC CCA TCC   720
226    Lys Gly Gln Pro Arg Glu Pro Gln Val Tyr Thr Leu Pro Pro Ser   240

721    CGG GAG GAG ATG ACC AAG AAC CAG GTC AGC CTG ACC TGC CTG GTC   765
241    Arg Glu Glu Met Thr Lys Asn Gln Val Ser Leu Thr Cys Leu Val   255

766    AAA GGC TTC TAT CCC AGC GAC ATC GCC GTG GAG TGG GAG AGC AAT   810
256    Lys Gly Phe Tyr Pro Ser Asp Ile Ala Val Glu Trp Glu Ser Asn   270

811    GGG CAG CCG GAG AAC AAC TAC AAG ACC ACG CCT CCC GTG CTG GAC   855
271    Gly Gln Pro Glu Asn Asn Tyr Lys Thr Thr Pro Pro Val Leu Asp   285
```

Figure 1B

```
856   TCC GAC GGC CCC TTC TTC CTC TAT AGC AAG CTC ACC GTG GAC AAG   900
286   Ser Asp Gly Pro Phe Phe Leu Tyr Ser Lys Leu Thr Val Asp Lys   300

901   AGC AGG TGG CAG CAG GGG AAC GTC TTC TCA TGC TCC GTG ATG CAT   945
301   Ser Arg Trp Gln Gln Gly Asn Val Phe Ser Cys Ser Val Met His   315

946   GAG GCT CTG CAC AAC CAC TAC ACG CAG AAG AGC CTC TCC CTG TCT   990
316   Glu Ala Leu His Asn His Tyr Thr Gln Lys Ser Leu Ser Leu Ser   330

991   CCG GGT AAA TAA   1002
331   Pro Gly Lys End
```

Figure 1B (continued)

VQLQQSGAELVKPGASVRLSCKASGYTFTEYIIHWIKLRSGQGLEWIGWFYPGSNDIQYN
AKFKGKATLTADKSSSTVYMELTGLTSEDSAVYFCARRDDFSGYDALPYWGQGTLVTVSA
ERKCCVECPPCPAPEFLGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSIEKTISK
AKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLGK

A

DIQMTQSPASLSVSVGETVTITCRTNENIYSNLAWYQQKQGKSPQLLIYAATHLVEGVPS
RFSGSGSGTQYSLKITSLQSEDFGNYYCQHFWGTPCTFGGGTKLEIKRERKCCVECPPCP
APEFLGGPSVFLFPPKPKDTLMISRTPEVTCVVVDVSQEDPEVQFNWYVDGVEVHNAKTK
PREEQFNSTYRVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLGK

B

Figure 8

SEQUENCE LISTING

```
<160> NUMBER OF SEQ ID NOS: 14

<210> SEQ ID NO 1
<211> LENGTH: 1041
<212> TYPE: DNA
<213> ORGANISM: Artificial Sequence
<220> FEATURE:
<223> OTHER INFORMATION: Chimeric construct
<220> FEATURE:
<221> NAME/KEY: CDS
<222> LOCATION: (1)..(1041)

<400> SEQUENCE: 1 gtc aag ctg cag cag tca gga gct gag ctg gtg aaa ccc ggg gcg tcg        48
Val Lys Leu Gln Gln Ser Gly Ala Glu Leu Val Lys Pro Gly Ala Ser
1               5                   10                  15 gtg agg ctg tcc tgc aag gcg tct ggt tac acc ttc act gaa tat att        96
Val Arg Leu Ser Cys Lys Ala Ser Gly Tyr Thr Phe Thr Glu Tyr Ile
            20                  25                  30 ata cac tgg ata aag ctg agg tct gga cag ggt ctt gag tgg att ggg       144
Ile His Trp Ile Lys Leu Arg Ser Gly Gln Gly Leu Glu Trp Ile Gly
        35                  40                  45 tgg ttt tac cct gga agt aat gat ata cag tac aat gcg aaa ttc aag       192
Trp Phe Tyr Pro Gly Ser Asn Asp Ile Gln Tyr Asn Ala Lys Phe Lys
    50                  55                  60 ggc aag gcc aca ttg act gcg gac aaa tcc tcc agc acc gtc tat atg       240
Gly Lys Ala Thr Leu Thr Ala Asp Lys Ser Ser Ser Thr Val Tyr Met
65                  70                  75                  80 gaa ctt act gga ttg aca tct gag gac tct gcg gtc tat ttc tgt gca       288
Glu Leu Thr Gly Leu Thr Ser Glu Asp Ser Ala Val Tyr Phe Cys Ala
                85                  90                  95 aga cgc gac gat ttc tct ggt tac gac gcc ctt cct tac tgg ggc caa       336
Arg Arg Asp Asp Phe Ser Gly Tyr Asp Ala Leu Pro Tyr Trp Gly Gln
            100                 105                 110 ggg acc atg gtc acc gtc tcc tca act gtg gct gca cca tct gct agc       384
Gly Thr Met Val Thr Val Ser Ser Thr Val Ala Ala Pro Ser Ala Ser
        115                 120                 125 cca gca cct gaa ctc ctg ggg gga ccg tca gtc ttc ctc ttc ccc cca       432
Pro Ala Pro Glu Leu Leu Gly Gly Pro Ser Val Phe Leu Phe Pro Pro
    130                 135                 140 aaa ccc aag gac acc ctc atg atc tcc cgg acc cct gag gtc aca tgc       480
Lys Pro Lys Asp Thr Leu Met Ile Ser Arg Thr Pro Glu Val Thr Cys
145                 150                 155                 160 gtg gtg gtg gac gtg agc cac gaa gac cct gag gtc aag ttc aac tgg       528
Val Val Val Asp Val Ser His Glu Asp Pro Glu Val Lys Phe Asn Trp
                165                 170                 175 tac gtg gac ggc gtg gag gtg cat aat gcc aag aca aag ccg cgg gag       576
Tyr Val Asp Gly Val Glu Val His Asn Ala Lys Thr Lys Pro Arg Glu
            180                 185                 190 gag cag tac aac agc acg tac cgt gtg gtc agc gtc ctc acc gtc ctg       624
```

-continued

```
                Glu Gln Tyr Asn Ser Thr Tyr Arg Val Val Ser Val Leu Thr Val Leu
                        195                 200                 205 cac cag gac tgg ctg aat ggc aag gag tac aag tgc aag gtc tcc aac       672
His Gln Asp Trp Leu Asn Gly Lys Glu Tyr Lys Cys Lys Val Ser Asn
    210                 215                 220 aaa gcc ctc cca gcc ccc atc gag aaa acc atc tcc aaa gcc aaa ggg       720
Lys Ala Leu Pro Ala Pro Ile Glu Lys Thr Ile Ser Lys Ala Lys Gly
225                 230                 235                 240 cag ccc cga gaa cca cag gtg tac acc ctg ccc cca tcc cgg gag gag       768
Gln Pro Arg Glu Pro Gln Val Tyr Thr Leu Pro Pro Ser Arg Glu Glu
                245                 250                 255 atg acc aag aac cag gtc agc ctg acc tgc ctg gtc aaa ggc ttc tat       816
Met Thr Lys Asn Gln Val Ser Leu Thr Cys Leu Val Lys Gly Phe Tyr
            260                 265                 270 ccc agc gac atc gcc gtg gag tgg gag agc aat ggg cag ccg gag aac       864
Pro Ser Asp Ile Ala Val Glu Trp Glu Ser Asn Gly Gln Pro Glu Asn
        275                 280                 285 aac tac aag acc acg cct ccc gtg ctg gac tcc gac ggc tcc ttc ttc       912
Asn Tyr Lys Thr Thr Pro Pro Val Leu Asp Ser Asp Gly Ser Phe Phe
    290                 295                 300 ctc tat agc aag ctc acc gtg gac aag agc agg tgg cag cag ggg aac       960
Leu Tyr Ser Lys Leu Thr Val Asp Lys Ser Arg Trp Gln Gln Gly Asn
305                 310                 315                 320 gtc ttc tca tgc tcc gtg atg cat gag gct ctg cac aac cac tac acg      1008
Val Phe Ser Cys Ser Val Met His Glu Ala Leu His Asn His Tyr Thr
                325                 330                 335 cag aag agc ctc tcc ctg tct ccg ggt aaa taa                          1041
Gln Lys Ser Leu Ser Leu Ser Pro Gly Lys
            340                 345
```

<210> SEQ ID NO 2
<211> LENGTH: 346
<212> TYPE: PRT
<213> ORGANISM: Artificial Sequence
<220> FEATURE:
<223> OTHER INFORMATION: Synthetic Construct

<400> SEQUENCE: 2

```
Val Lys Leu Gln Gln Ser Gly Ala Glu Leu Val Lys Pro Gly Ala Ser
1               5                   10                  15

Val Arg Leu Ser Cys Lys Ala Ser Gly Tyr Thr Phe Thr Glu Tyr Ile
            20                  25                  30

Ile His Trp Ile Lys Leu Arg Ser Gly Gln Gly Leu Glu Trp Ile Gly
        35                  40                  45

Trp Phe Tyr Pro Gly Ser Asn Asp Ile Gln Tyr Asn Ala Lys Phe Lys
    50                  55                  60

Gly Lys Ala Thr Leu Thr Ala Asp Lys Ser Ser Ser Thr Val Tyr Met
65                  70                  75                  80

Glu Leu Thr Gly Leu Thr Ser Glu Asp Ser Ala Val Tyr Phe Cys Ala
                85                  90                  95

Arg Arg Asp Asp Phe Ser Gly Tyr Asp Ala Leu Pro Tyr Trp Gly Gln
            100                 105                 110

Gly Thr Met Val Thr Val Ser Ser Thr Val Ala Ala Pro Ser Ala Ser
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160
```

```
Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
        180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 3
<211> LENGTH: 1005
<212> TYPE: DNA
<213> ORGANISM: Artificial Sequence
<220> FEATURE:
<223> OTHER INFORMATION: Chimeric construct
<220> FEATURE:
<221> NAME/KEY: CDS
<222> LOCATION: (1)..(1005)

<400> SEQUENCE: 3 gac atc cag atg acc cag tct cca gcc tcc cta tct gtt tct gtg gga      48
Asp Ile Gln Met Thr Gln Ser Pro Ala Ser Leu Ser Val Ser Val Gly
1               5                  10                  15 gaa act gtc acc atc acg tgt cga aca aat gaa aat att tac agt aat      96
Glu Thr Val Thr Ile Thr Cys Arg Thr Asn Glu Asn Ile Tyr Ser Asn
            20                  25                  30 tta gca tgg tat cag cag aaa cag gga aaa tct cct cag ctc ctg atc     144
Leu Ala Trp Tyr Gln Gln Lys Gln Gly Lys Ser Pro Gln Leu Leu Ile
        35                  40                  45 tat gct gca aca cac tta gta gag ggt gtg cca tca agg ttc agt ggc     192
Tyr Ala Ala Thr His Leu Val Glu Gly Val Pro Ser Arg Phe Ser Gly
    50                  55                  60 agt gga tca ggc aca cag tat tcc ctc aag atc acc agc ctg cag tct     240
Ser Gly Ser Gly Thr Gln Tyr Ser Leu Lys Ile Thr Ser Leu Gln Ser
65                  70                  75                  80 gaa gat ttt ggg aat tat tac tgt caa cac ttt tgg ggt act ccg tgc     288
Glu Asp Phe Gly Asn Tyr Tyr Cys Gln His Phe Trp Gly Thr Pro Cys
                85                  90                  95 acg ttc gga ggg ggg acc aag ctg gaa ata aaa cgg act gtg gct gca     336
Thr Phe Gly Gly Gly Thr Lys Leu Glu Ile Lys Arg Thr Val Ala Ala
            100                 105                 110 cca tct gct agc cca gca cct gaa ctc ctg ggg gga ccg tca gtc ttc     384
Pro Ser Ala Ser Pro Ala Pro Glu Leu Leu Gly Gly Pro Ser Val Phe
```

```
            115                 120                 125
ctc ttc ccc cca aaa ccc aag gac acc ctc atg atc tcc cgg acc cct       432
Leu Phe Pro Pro Lys Pro Lys Asp Thr Leu Met Ile Ser Arg Thr Pro
    130                 135                 140 gag gtc aca tgc gtg gtg gtg gac gtg agc cac gaa gac cct gag gtc       480
Glu Val Thr Cys Val Val Val Asp Val Ser His Glu Asp Pro Glu Val
145                 150                 155                 160 aag ttc aac tgg tac gtg gac ggc gtg gag gtg cat aat gcc aag aca       528
Lys Phe Asn Trp Tyr Val Asp Gly Val Glu Val His Asn Ala Lys Thr
                165                 170                 175 aag ccg cgg gag gag cag tac aac agc acg tac cgt gtg gtc agc gtc       576
Lys Pro Arg Glu Glu Gln Tyr Asn Ser Thr Tyr Arg Val Val Ser Val
            180                 185                 190 ctc acc gtc ctg cac cag gac tgg ctg aat ggc aag gag tac aag tgc       624
Leu Thr Val Leu His Gln Asp Trp Leu Asn Gly Lys Glu Tyr Lys Cys
        195                 200                 205 aag gtc tcc aac aaa gcc ctc cca gcc ccc atc gag aaa acc atc tcc       672
Lys Val Ser Asn Lys Ala Leu Pro Ala Pro Ile Glu Lys Thr Ile Ser
    210                 215                 220 aaa gcc aaa ggg cag ccc cga gaa cca cag gtg tac acc ctg ccc cca       720
Lys Ala Lys Gly Gln Pro Arg Glu Pro Gln Val Tyr Thr Leu Pro Pro
225                 230                 235                 240 tcc cgg gag gag atg acc aag aac cag gtc agc ctg acc tgc ctg gtc       768
Ser Arg Glu Glu Met Thr Lys Asn Gln Val Ser Leu Thr Cys Leu Val
                245                 250                 255 aaa ggc ttc tat ccc agc gac atc gcc gtg gag tgg gag agc aat ggg       816
Lys Gly Phe Tyr Pro Ser Asp Ile Ala Val Glu Trp Glu Ser Asn Gly
            260                 265                 270 cag ccg gag aac aac tac aag acc acg cct ccc gtg ctg gac tcc gac       864
Gln Pro Glu Asn Asn Tyr Lys Thr Thr Pro Pro Val Leu Asp Ser Asp
        275                 280                 285 ggc tcc ttc ttc ctc tat agc aag ctc acc gtg gac aag agc agg tgg       912
Gly Ser Phe Phe Leu Tyr Ser Lys Leu Thr Val Asp Lys Ser Arg Trp
    290                 295                 300 cag cag ggg aac gtc ttc tca tgc tcc gtg atg cat gag gct ctg cac       960
Gln Gln Gly Asn Val Phe Ser Cys Ser Val Met His Glu Ala Leu His
305                 310                 315                 320 aac cac tac acg cag aag agc ctc tcc ctg tct ccg ggt aaa taa          1005
Asn His Tyr Thr Gln Lys Ser Leu Ser Leu Ser Pro Gly Lys
                325                 330

<210> SEQ ID NO 4
<211> LENGTH: 334
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
                20                  25                  30

Leu Ala Trp Tyr Gln Gln Lys Gln Gly Lys Ser Pro Gln Leu Leu Ile
            35                  40                  45

Tyr Ala Ala Thr His Leu Val Glu Gly Val Pro Ser Arg Phe Ser Gly
        50                  55                  60

Ser Gly Ser Gly Thr Gln Tyr Ser Leu Lys Ile Thr Ser Leu Gln Ser
65                  70                  75                  80
```

```
Glu Asp Phe Gly Asn Tyr Tyr Cys Gln His Phe Trp Gly Thr Pro Cys
                 85                  90                  95
Thr Phe Gly Gly Gly Thr Lys Leu Glu Ile Lys Arg Thr Val Ala Ala
            100                 105                 110
Pro Ser Ala Ser Pro Ala Pro Glu Leu Leu Gly Gly Pro Ser Val Phe
        115                 120                 125
Leu Phe Pro Pro Lys Pro Lys Asp Thr Leu Met Ile Ser Arg Thr Pro
130                 135                 140
Glu Val Thr Cys Val Val Val Asp Val Ser His Glu Asp Pro Glu Val
145                 150                 155                 160
Lys Phe Asn Trp Tyr Val Asp Gly Val Glu Val His Asn Ala Lys Thr
                165                 170                 175
Lys Pro Arg Glu Glu Gln Tyr Asn Ser Thr Tyr Arg Val Val Ser Val
            180                 185                 190
Leu Thr Val Leu His Gln Asp Trp Leu Asn Gly Lys Glu Tyr Lys Cys
        195                 200                 205
Lys Val Ser Asn Lys Ala Leu Pro Ala Pro Ile Glu Lys Thr Ile Ser
    210                 215                 220
Lys Ala Lys Gly Gln Pro Arg Glu Pro Gln Val Tyr Thr Leu Pro Pro
225                 230                 235                 240
Ser Arg Glu Glu Met Thr Lys Asn Gln Val Ser Leu Thr Cys Leu Val
                245                 250                 255
Lys Gly Phe Tyr Pro Ser Asp Ile Ala Val Glu Trp Glu Ser Asn Gly
            260                 265                 270
Gln Pro Glu Asn Asn Tyr Lys Thr Thr Pro Pro Val Leu Asp Ser Asp
        275                 280                 285
Gly Ser Phe Phe Leu Tyr Ser Lys Leu Thr Val Asp Lys Ser Arg Trp
    290                 295                 300
Gln Gln Gly Asn Val Phe Ser Cys Ser Val Met His Glu Ala Leu His
305                 310                 315                 320
Asn His Tyr Thr Gln Lys Ser Leu Ser Leu Ser Pro Gly Lys
                325                 330

<210> SEQ ID NO 5
<211> LENGTH: 6
<212> TYPE: PRT
<213> ORGANISM: Artificial Sequence
<220> FEATURE:
<223> OTHER INFORMATION: Peptide linker

<400> SEQUENCE: 5

Thr Val Ala Ala Pro Ser
1               5

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
atatgctagc ccagcacctg aactcctg                                        28

<210> SEQ ID NO 7
<211> LENGTH: 25
<212> TYPE: DNA
<213> ORGANISM: Artificial Sequence
<220> FEATURE:
```

<223> OTHER INFORMATION: PCR primer

<400> SEQUENCE: 7
atattctaga ttatttaccc ggaga                                       25

<210> SEQ ID NO 8
<211> LENGTH: 40
<212> TYPE: DNA
<213> ORGANISM: Artificial Sequence
<220> FEATURE:
<223> OTHER INFORMATION: PCR primer

<400> SEQUENCE: 8
atatgctagc ggatccgata tcgtcaagct gcagcagtca                       40

<210> SEQ ID NO 9
<211> LENGTH: 46
<212> TYPE: DNA
<213> ORGANISM: Artificial Sequence
<220> FEATURE:
<223> OTHER INFORMATION: PCR primer

<400> SEQUENCE: 9
atatgctagc agatggtgca gccacagttg aggagacggt gaccat                46

<210> SEQ ID NO 10
<211> LENGTH: 40
<212> TYPE: DNA
<213> ORGANISM: Artificial Sequence
<220> FEATURE:
<223> OTHER INFORMATION: PCR primer

<400> SEQUENCE: 10
atatgctagc ggatccgata tcgacatcca gatgacccag                       40

<210> SEQ ID NO 11
<211> LENGTH: 48
<212> TYPE: DNA
<213> ORGANISM: Artificial Sequence
<220> FEATURE:
<223> OTHER INFORMATION: PCR primer

<400> SEQUENCE: 11
atatgctagc agatggtgca gccacagtcc gttttatttc cagcttgg              48

<210> SEQ ID NO 12
<211> LENGTH: 12
<212> TYPE: PRT
<213> ORGANISM: Homo sapiens

<400> SEQUENCE: 12

Glu Arg Lys Cys Cys Val Glu Cys Pro Pro Cys Pro
1               5                   10

<210> SEQ ID NO 13
<211> LENGTH: 349
<212> TYPE: PRT
<213> ORGANISM: Artificial Sequence
<220> FEATURE:
<223> OTHER INFORMATION: Chimeric protein

<400> SEQUENCE: 13

Val Gln Leu Gln Gln Ser Gly Ala Glu Leu Val Lys Pro Gly Ala Ser
1               5                   10                  15

Val Arg Leu Ser Cys Lys Ala Ser Gly Tyr Thr Phe Thr Glu Tyr Ile

```
                    20                  25                  30
    Ile His Trp Ile Lys Leu Arg Ser Gly Gln Gly Leu Glu Trp Ile Gly
                35                  40                  45

Trp Phe Tyr Pro Gly Ser Asn Asp Ile Gln Tyr Asn Ala Lys Phe Lys
     50                  55                  60

Gly Lys Ala Thr Leu Thr Ala Asp Lys Ser Ser Ser Thr Val Tyr Met
     65                  70                  75                  80

Glu Leu Thr Gly Leu Thr Ser Glu Asp Ser Ala Val Tyr Phe Cys Ala
                    85                  90                  95

Arg Arg Asp Asp Phe Ser Gly Tyr Asp Ala Leu Pro Tyr Trp Gly Gln
                100                 105                 110

Gly Thr Leu Val Thr Val Ser Ala Glu Arg Lys Cys Cys Val Glu Cys
                115                 120                 125

Pro Pro Cys Pro Ala Pro Glu Phe Leu Gly Gly Pro Ser Val Phe Leu
                130                 135                 140

Phe Pro Pro Lys Pro Lys Asp Thr Leu Met Ile Ser Arg Thr Pro Glu
    145                 150                 155                 160

Val Thr Cys Val Val Val Asp Val Ser Gln Glu Asp Pro Glu Val Gln
                        165                 170                 175

Phe Asn Trp Tyr Val Asp Gly Val Glu Val His Asn Ala Lys Thr Lys
                    180                 185                 190

Pro Arg Glu Glu Gln Phe Asn Ser Thr Tyr Arg Val Val Ser Val Leu
                195                 200                 205

Thr Val Leu His Gln Asp Trp Leu Asn Gly Lys Glu Tyr Lys Cys Lys
                210                 215                 220

Val Ser Asn Lys Gly Leu Pro Ser Ser Ile Glu Lys Thr Ile Ser Lys
    225                 230                 235                 240

Ala Lys Gly Gln Pro Arg Glu Pro Gln Val Tyr Thr Leu Pro Pro Ser
                        245                 250                 255

Gln Glu Glu Met Thr Lys Asn Gln Val Ser Leu Thr Cys Leu Val Lys
                    260                 265                 270

Gly Phe Tyr Pro Ser Asp Ile Ala Val Glu Trp Glu Ser Asn Gly Gln
                275                 280                 285

Pro Glu Asn Asn Tyr Lys Thr Thr Pro Pro Val Leu Asp Ser Asp Gly
                290                 295                 300

Ser Phe Phe Leu Tyr Ser Arg Leu Thr Val Asp Lys Ser Arg Trp Gln
    305                 310                 315                 320

Glu Gly Asn Val Phe Ser Cys Ser Val Met His Glu Ala Leu His Asn
                        325                 330                 335

His Tyr Thr Gln Lys Ser Leu Ser Leu Ser Leu Gly Lys
                    340                 345

<210> SEQ ID NO 14
<211> LENGTH: 337
<212> TYPE: PRT
<213> ORGANISM: Artificial Sequence
<220> FEATURE:
<223> OTHER INFORMATION: Chimeric protein

<400> SEQUENCE: 14

Asp Ile Gln Met Thr Gln Ser Pro Ala Ser Leu Ser Val Ser Val Gly
 1               5                  10                  15

Glu Thr Val Thr Ile Thr Cys Arg Thr Asn Glu Asn Ile Tyr Ser Asn
                20                  25                  30

Leu Ala Trp Tyr Gln Gln Lys Gln Gly Lys Ser Pro Gln Leu Leu Ile
```

```
                35                  40                  45
Tyr Ala Ala Thr His Leu Val Glu Gly Val Pro Ser Arg Phe Ser Gly
        50                  55                  60
Ser Gly Ser Gly Thr Gln Tyr Ser Leu Lys Ile Thr Ser Leu Gln Ser
65                  70                  75                  80
Glu Asp Phe Gly Asn Tyr Tyr Cys Gln His Phe Trp Gly Thr Pro Cys
                85                  90                  95
Thr Phe Gly Gly Gly Thr Lys Leu Glu Ile Lys Arg Glu Arg Lys Cys
            100                 105                 110
Cys Val Glu Cys Pro Pro Cys Pro Ala Pro Glu Phe Leu Gly Gly Pro
            115                 120                 125
Ser Val Phe Leu Phe Pro Pro Lys Pro Lys Asp Thr Leu Met Ile Ser
        130                 135                 140
Arg Thr Pro Glu Val Thr Cys Val Val Val Asp Val Ser Gln Glu Asp
145                 150                 155                 160
Pro Glu Val Gln Phe Asn Trp Tyr Val Asp Gly Val Glu Val His Asn
                165                 170                 175
Ala Lys Thr Lys Pro Arg Glu Glu Gln Phe Asn Ser Thr Tyr Arg Val
            180                 185                 190
Val Ser Val Leu Thr Val Leu His Gln Asp Trp Leu Asn Gly Lys Glu
        195                 200                 205
Tyr Lys Cys Lys Val Ser Asn Lys Gly Leu Pro Ser Ser Ile Glu Lys
210                 215                 220
Thr Ile Ser Lys Ala Lys Gly Gln Pro Arg Glu Pro Gln Val Tyr Thr
225                 230                 235                 240
Leu Pro Pro Ser Gln Glu Glu Met Thr Lys Asn Gln Val Ser Leu Thr
                245                 250                 255
Cys Leu Val Lys Gly Phe Tyr Pro Ser Asp Ile Ala Val Glu Trp Glu
            260                 265                 270
Ser Asn Gly Gln Pro Glu Asn Asn Tyr Lys Thr Thr Pro Pro Val Leu
            275                 280                 285
Asp Ser Asp Gly Ser Phe Phe Leu Tyr Ser Arg Leu Thr Val Asp Lys
        290                 295                 300
Ser Arg Trp Gln Glu Gly Asn Val Phe Ser Cys Ser Val Met His Glu
305                 310                 315                 320
Ala Leu His Asn His Tyr Thr Gln Lys Ser Leu Ser Leu Ser Leu Gly
                325                 330                 335
Lys
```

RECOMBINANT MONOVALENT ANTIBODIES

SEQUENCE LISTING SUBMISSION VIA EFS-WEB

A computer readable text file, entitled "SequenceListing.txt," created on or about Jul. 13, 2011 with a file size of about 23 kb contains the sequence listing for this application and is hereby incorporated by reference in its entirety.

The invention relates to recombinant monovalent antibodies, in particular IgG antibodies, and to their therapeutic uses.

An antibody (immunoglobulin) molecule is a Y-shaped tetrameric protein composed of two heavy (H) and two light (L) polypeptide chains held together by covalent disulfide bonds and noncovalent interactions.

Each light chain is composed of one variable domain (VL) and one constant domain (CL). Each heavy chain has one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG).

The variable domains show considerable variation in amino acid composition from one antibody to another. Each of the VH and the VL variable domains comprises three regions of extreme variability, which are termed the complementarity-determining regions (CDRs), separated by less variable regions called the framework regions (FRs). The non-covalent association between the VH and the VL region forms the Fv fragment (for "fragment variable") which contains one of the two antigen-binding sites of the antibody. ScFv fragments (for single chain fragment variable), which can be obtained by genetic engineering, associates in a single polypeptide chain the VH and the VL region of an antibody, separated by a peptide linker.

Other functional immunoglobulin fragments can be obtained by proteolytic fragmentation of the immunoglobulin molecule. Papain treatment splits the molecule into three fragments: two heterodimeric Fab fragments (for 'fragment antigen binding'), each associating the VL and CL domains of the light chain with the VH and CH1 domains of the heavy chain, and one homodimeric Fc fragment (for "fragment crystalline"), which comprises the CH2 and CH3 (and eventually CH4) domains of the light chain. Pepsin treatment produces the F(ab)'2 fragment which associates two Fab fragments, and several small fragments.

The Fc fragment does not bind the antigen, but is responsible for the effector functions of the antibody, including in particular binding to Fc receptors and complement fixation. The Fv, Fab, and F(ab)'2 fragments retain the antigen-binding ability of the whole antibody. However, the F(ab)'2 fragments, like the whole immunoglobumin molecule, are divalent (i.e. they contain two antigen binding sites and can bind and precipitate the antigen), while the Fv and Fab fragments are monovalent (they contain one antigen binding site, and can bind but cannot precipitate the antigen).

Antibodies directed against cell-surface receptors are of great interest for the development of therapeutic agents for various disorders and diseases. They are generally used for their properties to mimic the structure of a biological ligand of a target receptor. In some cases this structural similarity may result in agonistic effects leading to the activation of the target receptor; in other cases it may result in antagonistic effects, leading to the blocking of the target receptor.

However, many antibodies having antagonistic properties when used as monovalent fragments may also show agonistic effects when used as full length antibodies. These agonistic effects result from the bivalency of the full-length antibodies, which induces the crosslinking of the target receptors on the cell surface, leading to receptor activation. This phenomenon is unwanted when the desired therapeutic activity relies upon an antagonistic effect. Examples of receptors that are activated by crosslinking include CD28, CD3 (DAMLE et al., J. Immunol., 140, 1753-61, 1988; ROUTLEDGE et al., Eur J Immunol, 21, 2717-25, 1991), TNF receptors, etc . . . .

The monovalent forms of antagonistic antibodies, such as Fab or scFv fragments, are devoid of agonistic activity. Therefore, they are useful therapeutic agents to block a cell receptor without inducing its cross-linking. However, their therapeutic use is hampered by their short half-life in vivo; they are eliminated within minutes and would require a continuous administration. To overcome this problem, it has been proposed to fuse these monovalent fragments with large molecules such as water-soluble proteins (PCT WO02051871) or polyethylene glycol (BLICK & CURRAN, BioDrugs, 21, 195-201; discussion 02-3, 2007).

Another approach for producing monovalent antibodies has been to construct fusion proteins associating one Fab fragment (i.e an heterodimer comprising the VL and the CL regions of the light chain, and the VH and the CH1 region of the heavy chain) with one Fc fragment (i.e an homodimer comprising the CH2 and CH3 regions of the heavy chains). ROUTLEDGE et al. (ROUTLEDGE et al., Eur J Immunol, 21, 2717-25, 1991) describe the construction of a monovalent antibody by introduction into an antibody-producing cell of a truncated Ig heavy chain gene encoding only the hinge, CH2 and CH3 domains; the expression of this gene in the antibody producing cell results in N-terminally truncated heavy chains (devoid of the VH and CH1 domains) which can either associate between them to form Fc molecules, or with full length heavy chains produced by the antibody producing cell to form a monovalent antibody molecules comprising a full-length light chain, a full-length heavy chain, and a N-terminally truncated heavy chain. PCT WO 2007/048037 describes monovalent antibodies which are heterodimers resulting from the association of an immunoglobulin heavy chain with a fusion protein comprising an immunoglobulin light chain and a Fc molecule.

An advantage of this approach is that the resulting antibodies contain an IgG Fc domain, which in some cases, is useful if one desires to retain some of the effector functions of the IgG molecule, and which also allows to target the molecule to the neonatal Fc receptor (FcRn) expressed by endothelial cells. This receptor actively traps several macromolecules, including antibodies, inside the blood stream conferring them an extended serum half-live. The binding of IgG molecules to this receptor facilitates their transport, and allows their protection from degradation.

The IgG Fc domain of immunoglobulins has also been utilized to form fusion proteins with molecules other than antibodies, for instance cytokines, growth factors, soluble growth factors, allowing to extend their half-life in the bloodstream, and also to deliver them by non-invasive routes, for instance by pulmonary administration (DUMONT et al., BioDrugs, 20, 151-60, 2006).

In the case of monovalent antibodies, the fusion proteins containing the IgG Fc domain which have been described until now also comprise the CL and/or the CH1 region. It is generally believed that these regions, which are part of the Fab fragment, play an important part in the correct assembly of the IgG molecule, and can also influence the antigen/antibody interaction.

As indicated above, one of the cell surface receptors known to be stimulated after its engagement by bivalent antibodies, and which can be efficiently blocked by certain monovalent fragments of some antibodies, is the CD28 receptor. By way of example, it has been shown that it was possible to efficiently block CD28 with Fab fragments or with a fusion protein comprising a scFv fragment of the anti-CD28 monoclonal antibody CD28.3, fused with alphal-antitrypsin (VANHOVE et al., Blood, 102, 564-70, 2003). This approach demonstrated an efficacy in vitro as well as in organ transplantation in mice and in primates (POIRIER et al., World Transplant Congress, Sydney, Australia. Aug. 16-21, 2008).

The inventors have sought to further improve the pharmacokinetics properties of monovalent fragments of CD28.3. With this purpose, they have first attempted to construct a recombinant monovalent antibody similar to those disclosed in the prior art, by fusing the each of the VH and VL domains of CD28.3 to the CH1-CH2-CH3 domains of an heterologous IgG molecule. However this attempt failed to result in a protein with the required antibody activity.

The inventors then tried to remove the CH1 domains of these fusion proteins and found that the resulting monovalent antibody was secreted and active, and that it behaves in vitro like its corresponding Fab fragment. Further, after intravenous injection in mice, it showed an elimination half-live that was significantly longer than Fab fragments and not significantly different from IgG antibodies.

These results show that combining the variable domains of a monoclonal antibody with only the CH2-CH3 domains rather than with all the constant domains of an IgG molecule allows to obtain a functional monovalent antibody, having the prolonged in vivo half-live that is conferred by the presence of an Fc fragment. This format can be used to generate therapeutic antibodies in all cases where monovalent binding to a ligand, for instance a cellular receptor, is required.

Therefore, an object of the present invention is a recombinant monovalent antibody derived from a parent antibody directed against an antigen of interest, wherein said recombinant antibody is an heterodimer of:

a first protein chain consisting essentially of, from its N-terminus to its C-terminus:

a region A having the structure of the VH domain of an immunoglobulin, said region A comprising the CDRs of the heavy chain of said parent antibody;

a region B consisting of a peptide linker and the CH2 and CH3 domains of an IgG immunoglobulin;

a second protein chain consisting essentially of, from its N-terminus to its C-terminus:

a region A' having the structure of the VL domain of an immunoglobulin, said region A' comprising the CDRs of the light chain of said parent antibody;

a region B identical to the region B of the first polypeptide.

The parent antibody can be any antibody directed against the antigen of interest; it can be a native monoclonal antibody; it can also be a recombinant or synthetic antibody, such as a chimeric antibody, a humanized antibody, or an antibody originating from phage-display or ribosome display technologies.

A region having the structure of the VH or of the VL domain of an immunoglobulin comprises, as indicated above, four framework regions (FRs), connected by three hypervariable regions or complementarity determining regions (CDRs) which are involved in antigen recognition specificity. In a recombinant monovalent antibody of the invention, regions A and A' can consist of the native VH or VL domains of the parent antibody; however, they can also be obtained by incorporating the CDRs of the parent antibody into the framework regions (FRs) of another antibody, in particular of an antibody of human origin, using techniques, known in themselves, of CDR grafting.

The peptide linker of region B may comprises from 0 to 16 amino acids. It comprises preferably 5 to 7 amino acids. Examples of suitable peptide linkers are those which are used in the construction of scFv fragments, such are those disclosed for instance by FREUND et al. (FEBS Lett. 320, 97-100, 1993) or by SHAN et al. (J Immunol. 162, 6589-95, 1999).

Said peptide linker may be devoid of cysteine residues, or may comprise one or more cysteine residue(s). A peptide linker devoid of cysteine residues will be preferred if the monovalent antibody is to be produced in the $E.$ $coli$ periplasm. An example of a peptide linker devoid of cysteine residues is a peptide having the sequence TVAAPS (SEQ ID NO: 5).

Alternatively, a peptide linker comprising cysteine residues allows the formation of inter-chain disulfide bonds, which help to stabilize the heterodimer. As a peptide linker comprising cysteine residues, one can use for instance the hinge region of a naturally occurring IgG. A preferred hinge region is the hinge region of IgG2 immunoglobulins having the sequence ERKCCVECPPCP (SEQ ID NO: 12), which provides a high stability.

The CH2 and CH3 domains are preferably those of an immunoglobulin of human origin of the IgG isotype. Said IgG can belong to any of the IgG subclasses (IgG1, IgG2, IgG3 or IgG4). Preferably, it belongs to the IgG1 subclass or the IgG4 subclass.

Besides the essential constituents listed above, the first and/or the second protein chain can further comprise one or more optional polypeptide sequence(s) which is (are) not involved in the biological properties of the recombinant monovalent antibody, but may facilitate its detection or purification. For instance said polypeptide sequence can be a tag polypeptide, such as a streptavidin-binding peptide, an hexa-histidine ($His_6$) tag, or a FLAG-tag.

The first and/or the second protein chain can be glycosylated or not.

According to a particular embodiment of the invention, the parent antibody is the monoclonal antibody CD28.3, produced by the hybridoma CNCM I-2582. The hybridoma CNCM I-2582 is disclosed in PCT WO02051871, and has been deposited, according to the terms of the Treaty of Budapest, on Nov. 28, 2000, with the CNCM (Collection Nationale de Cultures de Microorganismes, 25 rue du Docteur Roux, 75724 PARIS CEDEX 15).

A particular example of a recombinant monovalent antibody of the invention, which is described in detail in the Examples below, is an antibody wherein the polypeptide sequence of the first protein chain is SEQ ID NO: 2, and the polypeptide sequence of the second protein chain is SEQ ID NO: 4. Another example of a recombinant monovalent antibody of the invention, is an antibody wherein the polypeptide sequence of the first protein chain is SEQ ID NO: 13, and the polypeptide sequence of the second protein chain is SEQ ID NO: 14.

Another object of the invention is a polynucleotide comprising a sequence encoding the first protein chain and/or a sequence encoding the second protein chain of a recombinant monovalent antibody of the invention. Said polynucleotides may also comprise additional sequences: for instance they may advantageously comprise a sequence encoding a leader sequence or signal peptide allowing secretion of said protein chain. They may optionally also comprise one or more sequence(s) encoding one or more tag polypeptide(s).

The present invention also encompasses recombinant vectors, in particular expression vectors, comprising a polynucleotide of the invention, associated with transcription- and translation-controlling elements which are active in the host cell chosen. Vectors which can be used to construct expression vectors in accordance with the invention are known in themselves, and will be chosen in particular as a function of the host cell intended to be used.

The present invention also encompasses host-cells transformed with a polynucleotide of the invention. Preferably, said host cell is transformed with a polynucleotide comprising a sequence encoding the first protein chain of a recombinant monovalent antibody of the invention and a polynucleotide comprising a sequence encoding the second protein chain of a recombinant monovalent antibody of the invention, and expresses said recombinant antibody. Said polynucleotides can be inserted in the same expression vector, or in two separate expression vectors.

Host cells which can be used in the context of the present invention can be prokaryotic or eukaryotic cells. Among the eukaryotic cells which can be used, mention will in particular be made of plant cells, cells from yeast, such as *Saccharomyces*, insect cells, such as *Drosophila* or *Spodoptera* cells, and mammalian cells such as HeLa, CHO, 3T3, C127, BHK, COS, etc., cells.

The construction of expression vectors of the invention and the transformation of the host cells can be carried out by the conventional techniques of molecular biology.

Still another objet of the invention is a method for preparing a recombinant monovalent antibody of the invention, Said method comprises culturing an host-cell transformed with a polynucleotide comprising a sequence encoding the first protein chain of a recombinant monovalent antibody of the invention, and with a polynucleotide comprising a sequence encoding the second protein chain of a recombinant monovalent antibody of the invention, and recovering said recombinant monovalent antibody from said culture.

If the protein is secreted by the host-cell, it can be recovered directly from the culture medium; if not, cell lysis will be carried out beforehand. The protein can then be purified from the culture medium or from the cell lysate, by conventional procedures, known in themselves to those skilled in the art, for example by fractionated precipitation, in particular precipitation with ammonium sulfate, electrophoresis, gel filtration, affinity chromatography, etc.

A subject of the invention is also a method for producing a protein in accordance with the invention, characterized in that it comprises culturing at least one cell in accordance with the invention, and recovering said protein from said culture.

The recombinant monovalent antibodies of the invention can be used to obtain medicinal products. These medicinal products are also part of the object of the invention.

For instance, recombinant monovalent antibodies of the invention derived from the parent antibody CD28.3 can be used to obtain immunosuppressant medicinal products which selectively blocks T cell activation phenomena involving the CD28 receptor. Such immunosuppressant medicinal products which act by selective blocking of CD28 have applications in all T lymphocyte-dependent pathological conditions, including in particular transplant rejection, graft-versus-host disease, T lymphocyte-mediated autoimmune diseases, such as type I diabetes, rheumatoid arthritis or multiple sclerosis, and type IV hypersensitivity, which is involved in allergic phenomena and also in the pathogenesis of chronic inflammatory diseases, in particular following infection with a pathogenic agent (in particular leprosy, tuberculosis, leishmaniasis, listeriosis, etc.).

The present invention will be understood more clearly from the further description which follows, which refers to nonlimiting examples of the preparation and properties of a recombinant monovalent antibody (hereafter referred to as Mono28Fc) in accordance with the invention.

LEGENDS OF THE DRAWINGS

Figure 1D:
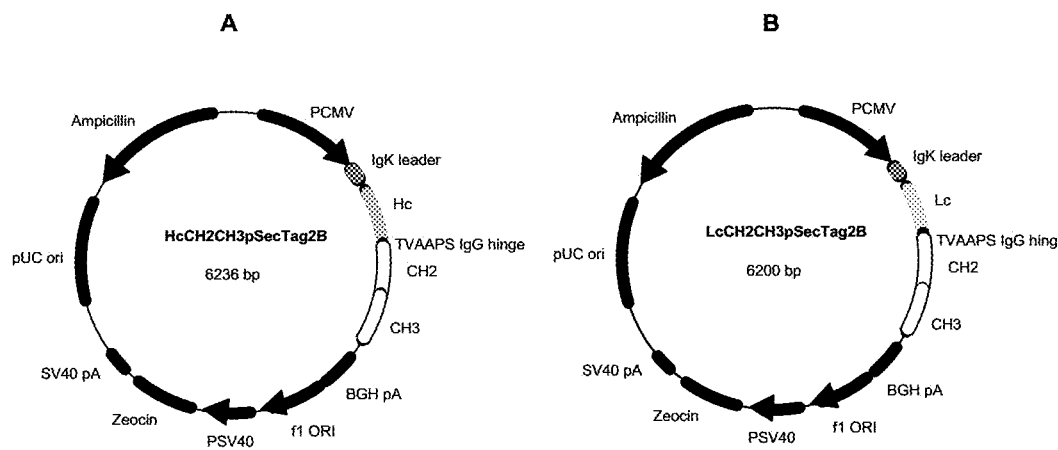
Figure 2:
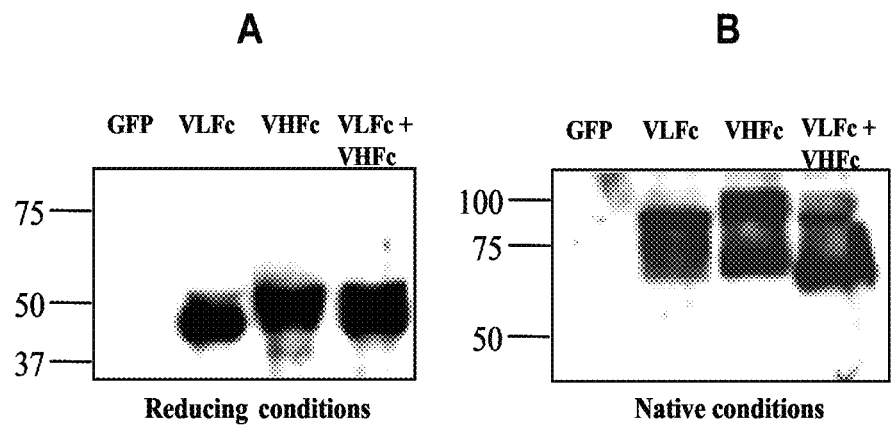
Figure 3:
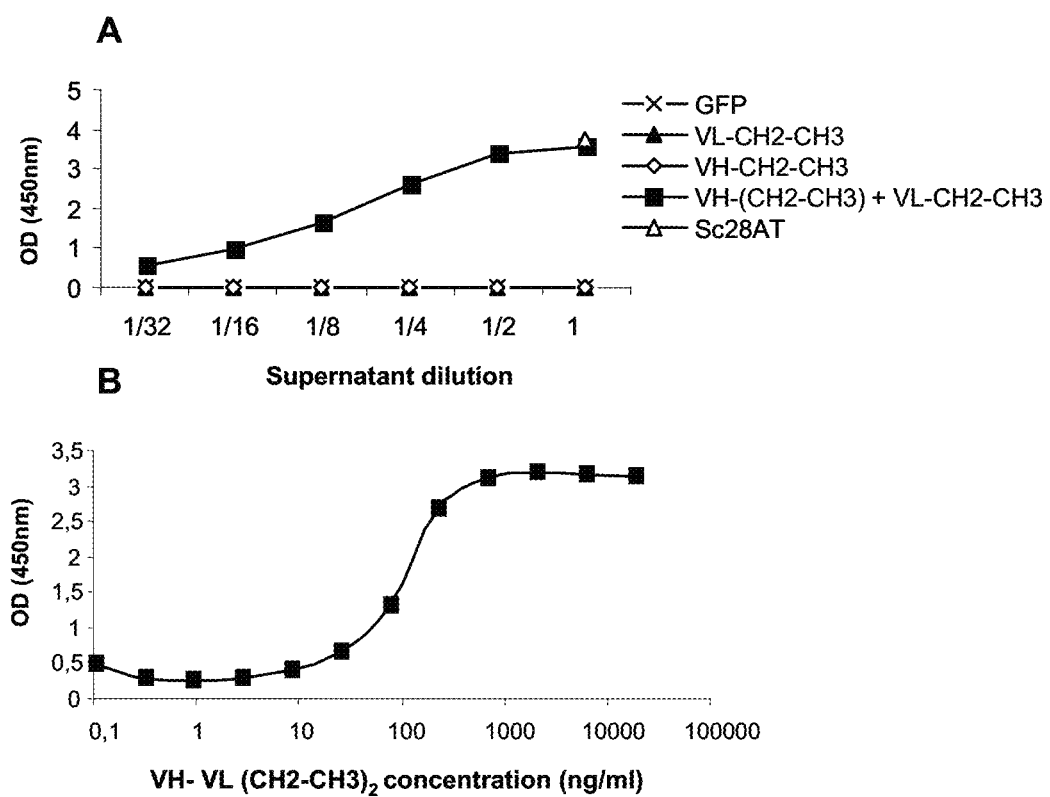

FIG. 1A: Nucleotidic and amino acid sequence of Mono28Fc, VH-CH2CH3 chain.
Underlined: VH domain. Bold: linker. Double underlining: IgG1 CH2-CH3 domains.
FIG. 1B: Nucleotidic and amino acid sequence of Mono28Fc, VL-CH2CH3 chain.
Underlined: VL domain. Bold: linker. Double underlining: IgG1 CH2-CH3 domains.
FIG. 1C: Molecular constructions allowing the expression of Mono28Fc after transfection into eukaryotic host cells.
pCMV: promoter of the cytomegalovirus. Igk leader: signal sequence from the mouse immunoglobulin kappa light chain. VH: variable domain of the heavy chain of the CD28.3 antibody. VL: variable domain of the light chain of the CD28.3 antibody. CH2 and CH3 represent the corresponding domains of the IgG1 human immunoglobulin.
FIG. 1D: Expression plasmids for the synthesis of Mono28Fc in eukaryotic cells.
A: plasmid for the synthesis of the VH(Hc)-CH2-CH3 protein. B: plasmid for the synthesis of the VL(Lc)-CH2-CH3 protein. pCMV: promoter of the cytomegalovirus. Igk leader: signal sequence from the mouse immunoglobulin kappa light chain. Hc: VL variable domain of the heavy chain of the CD28.3 antibody. Lc: VL variable domain of the light chain of the CD28.3 antibody. CH2 and CH3 represent the corresponding domains of the IgG1 human immunoglobulin. BGH pA: signal for the initiation of the 3' polyadenylation of the mRNA molecule, from the bovine growth hormone. Zeocin, ampicillin: resistance genes for the corresponding antibiotic.
FIG. 2: Western blot analysis of pSecVHFc and pSecVLFc expression.
A: Supernatants from Cos cells transfected with the indicated plasmids were collected and reduced before analysis by 10 min. incubation at 100° C. with 10 mM DTT. B: no reduction. Molecular weights are indicated on the left sides.
FIG. 3: Activity ELISA. Recombinant CD28 was immobilized on microtitration plates.
A: Supernatants from control, transfected or co-transfected Cos cells were added at the indicated dilutions, washed and revealed with rabbit anti-VHNL antibodies plus anti-rabbit immunoglobulins-HRP. GFP: negative control; transfection with an irrelevant GFP plasmid. Sc28AT: positive control; transfection with a plasmid coding for a single-chain Fv against CD28. VLFc: transfection with the pSec-VLFc plasmid. VHFc: transfection with the pSec-VHFc plasmid. VH-(CH2-CH3)+VL-CH2-CH3: co-transfection with the pSec-VLFc and the pSec-VHFc plasmids. B: Binding ELISA on recombinant CD28 of purified Mono28Fc molecules at the indicated concentration. Revelation is as in A. Dots are means of triplicates.

Figure 4:
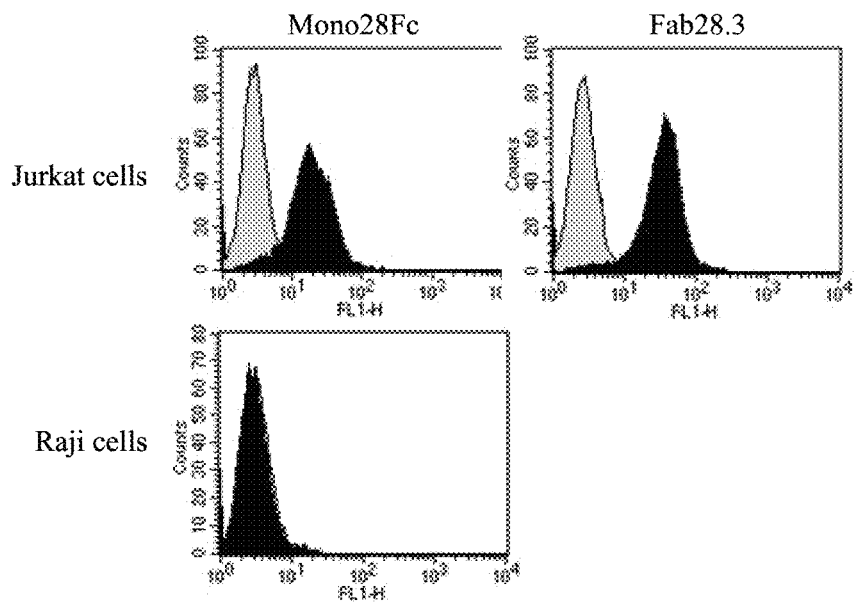

FIG. 4: Flow cytometry.

CD28+ Jurkat T cells and CD28− Raji B cells were incubated with purified Mono28Fc or with CD28.3 Fab fragments at 10 µg/ml for 30 min. at 4° C., washed and revealed with rabbit anti-VHNH antibodies plus FITC-labeled goat anti-rabbit immunoglobulins (black profiles). As a control, cells were incubated with rabbit anti-VHNH antibodies plus FITC-labeled goat anti-rabbit immunoglobulins only (grey profiles). Cells were then washed, fixed and analyzed by Facs.

Figure 5:
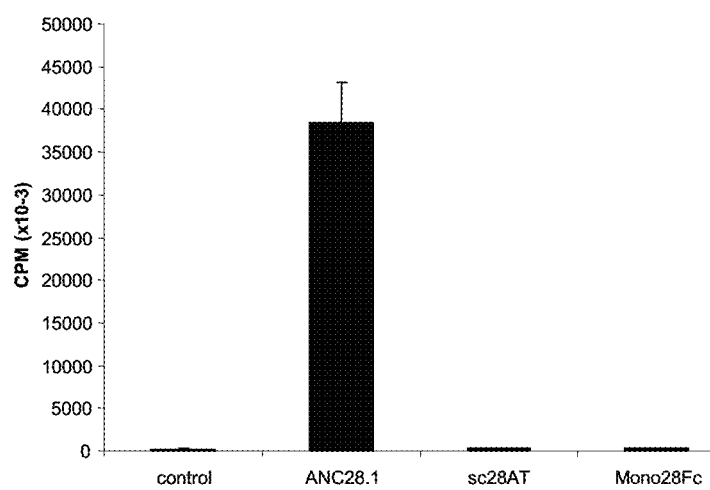

FIG. 5: Activation assay.

Human PBMC ($10^5$/well) were cultivated in medium or in medium plus 10 µg/ml Mono28Fc, sc28AT monovalent antibodies or with ANC28.1 superagonist antibodies for 3 days. 0.5 µCi $^3$H-tymidine was added for the last 16 h of the culture. Incorporated radioactivity was evaluated on a scintillation counter after transfer on nitrocellulose membranes.

Figure 6:
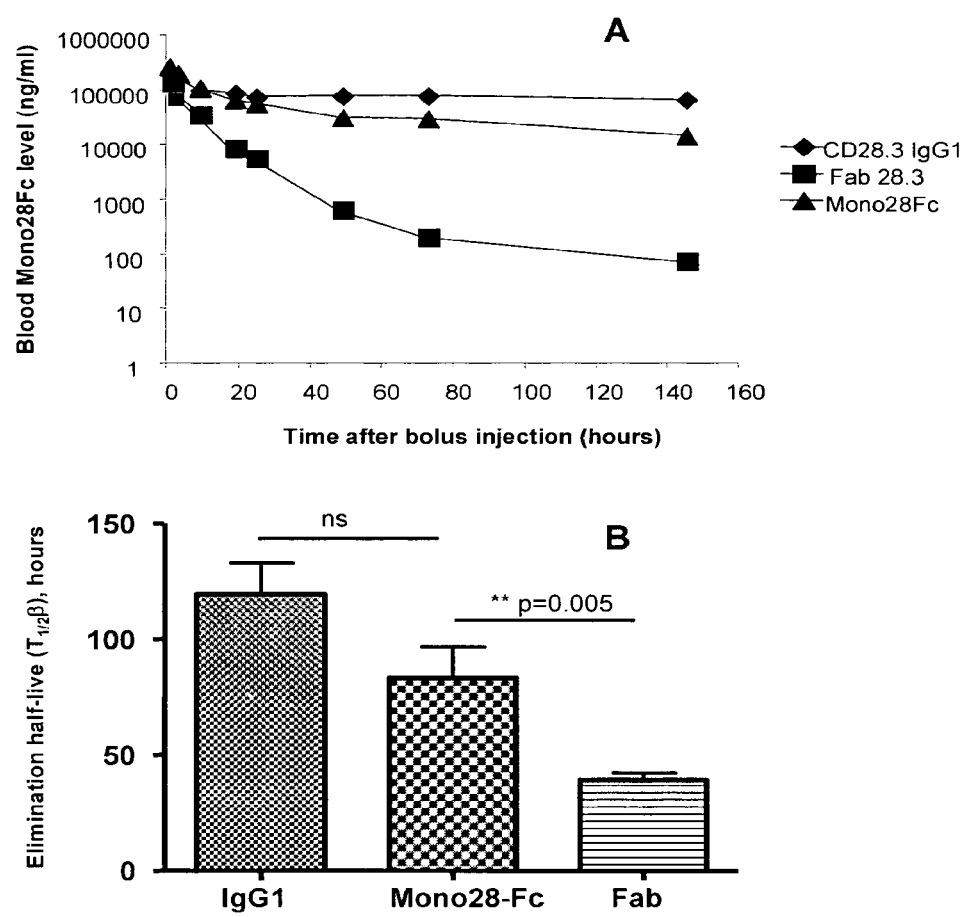

FIG. 6: Pharmacokinetic in mice.

A: Indicated proteins were injected i.v. into swiss mice and blood samples were collected after the indicated time points. CD28 binding activity was measured by ELISA. N=4 for each point, dots are means of the 4 measurements. B: Elimination half-lives ($T_{1/2}\beta$) were calculated from the curves in A.

Figure 7:
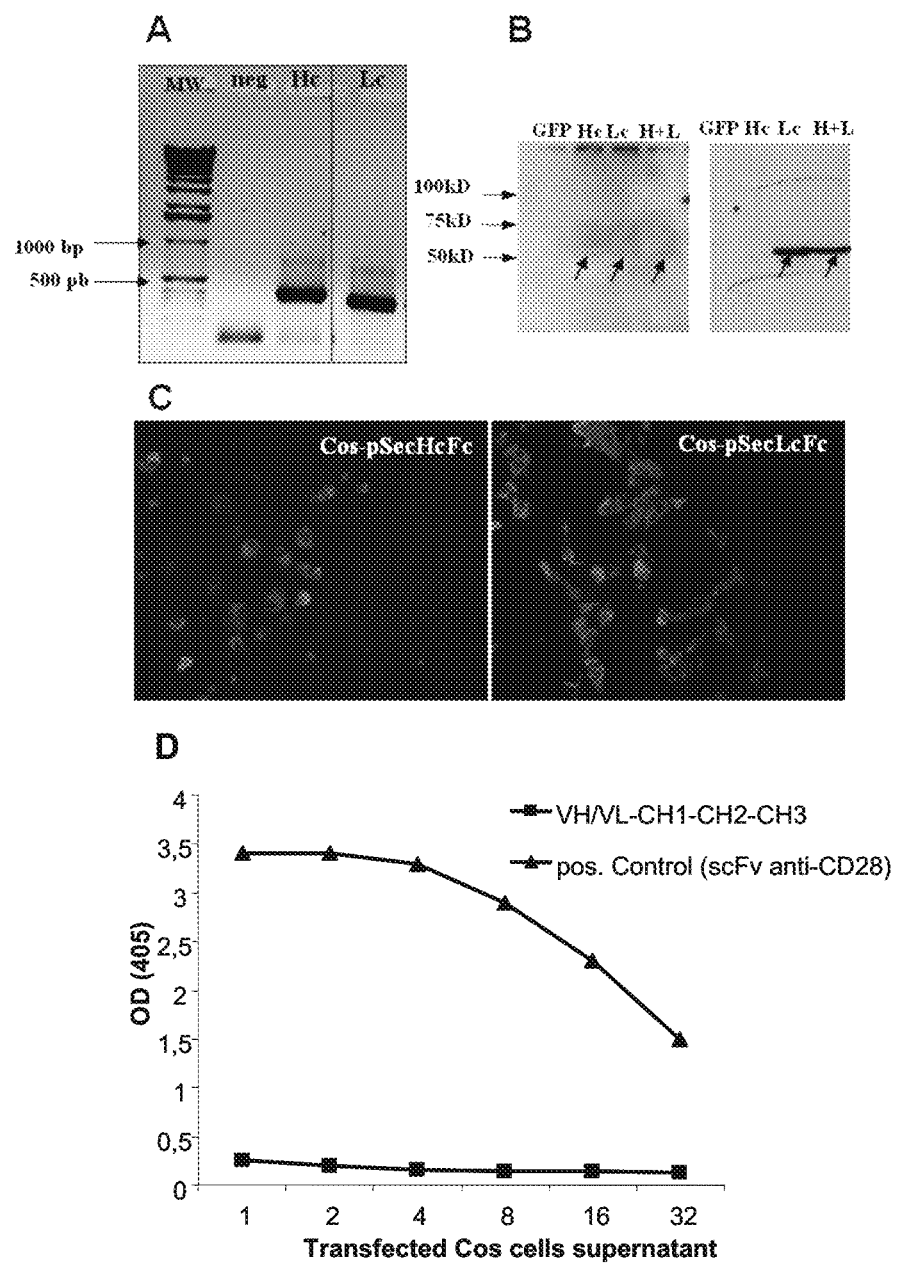

FIG. 7: Molecular constructions combining VH, VL with CH1-CH2-CH3 are non-functional.

A: RT-PCR analysis of the VH and VL mRNA chains expression after transfection of Cos cells. B: Western blot analysis of supernatants (right panel) and lysates (left panel) of Cos cell transfected with pSecVH-CH1-CH2-CH3 and pSecVL-CH1-CH2-CH3 plasmids. Revelation was performed as in FIG. 2. C: Immunofluorescence analysis of Cos cells transfected with pSec-VH-CH1-CH2-CH3 and pSec-VL-CH1-CH2-CH3; revelation with rabbit anti-VH/VL antibody plus anti-PE. Magnification: 20×. D: Activity ELISA of supernatants of Cos cell co-transfected with pSecVH-CH1-CH2-CH3 and pSecVL-CH1-CH2-CH3. Revelation was performed as in FIG. 3.

FIG. 8: Amino acid sequence of Mono28Fc with IgG2 hinge and IgG4 CH2CH3 domains.

A: VH-CH2CH3 chain: Underlined: VH domain. Bold: linker. Double underlining: IgG4 CH2-CH3 domains.

B: VL-CH2CH3 chain: Underlined: VL domain. Bold: linker. Double underlining: IgG4 CH2-CH3 domains.

EXAMPLE 1: CONSTRUCTION OF THE MONOVALENT ANTIBODY MONO28FC

The CH2-CH3 domains of a human IgG1 gene (NCBI Accession BC018747) was amplified using the following primers introducing NheI/XbaI sites: CH2CH3-5':

```
CH2CH3-5':
                                       (SEQ ID NO: 6)
5'-ATATGCTAGCCCAGCACCTGAACTCCTG-3';

CH2CH3-3':
                                       (SEQ ID NO: 7)
5'-ATATTCTAGATTATTTACCCGGAGA-3'.
```

The resulting fragment was introduced into the pSC-A vector (Stratagene, Amsterdam, The Netherlands), resulting in the pSC-A-CH2-CH3 vector.

VH and VL domains corresponding to the CD28.3 antibody anti-human CD28 were amplified from the previously described CNCM 1-2762 scFv cDNA (VANHOVE et al., Blood, 102, 564-70, 2003) and NheI cloning sites were introduced by PCR with the following primers: VH:

```
VH:
Hc28.3-5':
                                       (SEQ ID NO: 8)
5'-ATATGCTAGCGGATCCGATATCGTCAAGCTGCAGCAGTCA-3';

Hc28.3-3':
                                       (SEQ ID NO: 9)
5'-ATATGCTAGCAGATGGTGCAGCCACAGTTGAGGAGACGGTGACCA
T-3';

VL:
Lc28.3-5':
                                       (SEQ ID NO: 10)
5'-ATATGCTAGCGGATCCGATATCGACATCCAGATGACCCAG-3';

Lc28.3-3':
                                       (SEQ ID NO: 11)
5'-ATATGCTAGCAGATGGTGCAGCCACAGTCCGTTTTATTTCCAGCTTG
G-3'.
```

The VH and VL fragments were cloned individually 5' to the CH2-CH3 domains into the NheI site of the pSC-A-CH2-CH3 vector, resulting in VH-pSC-A-CH2-CH3 and VL-pSC-A-CH2-CH3 plasmids. The nucleotidic and amino acid sequences of the resulting VH-CH2CH3 and VL-CH2CH3 constructs are indicated respectively on FIGS. 1A and 1B. They are also indicated as SEQ ID NO: 1 and 3.

Each construct was then subcloned in the EcoRV restriction site of the pSecTag2B eukaryotic pCMV-based expression plasmid (Invitrogen, Cergy Pontoise, France), enabling a fusion at the N-terminus with the secretion signal from the V-J2-C region of the mouse Ig kappa-chain provided by the pSecTag2 vector. The constructs were proofread by sequencing. The resulting expression cassettes and the plasmids pSec-VH-Fc(CH2-CH3) and pSec-VL-Fc(CH2-CH3) containing these constructs are schematized respectively on FIGS. 1C and 1D.

EXAMPLE 2: EUCARYOTIC EXPRESSION OF MONO28FC

COS cells were transfected separately with pSec-VH-Fc(CH2-CH3) (VH-Fc) or pSec-VL-Fc(CH2-CH3) (VL-Fc), or co-transfected with pSec-VH-Fc(CH2-CH3) and pSec-VL-Fc(CH2-CH3) or, as a control, transfected with a plasmid coding for an irrelevant green fluorescent protein (GFP), using the Fugene lipofection kit (Roche Diagnostics, Basel, Switzerland) according to the manufacturer's instructions. Cultures were maintained for 3 days at 37° C., divided one third, and put back into culture for an additional 3 days, after which time the cell supernatants were collected, electrophoresed in 10% polyacrylamide gels and blotted onto nitrocellulose membranes.

Blots were revealed with rabbit anti-CD28.3VH/VL (1:5000 dilution) and an HRP-conjugated donkey antirabbit Ig antibody (Jackson Immuno-Research Laboratories) and developed by chemiluminescence (Amersham Pharmacia Biotech).

The results are shown on FIG. 2. Immunoreactive proteins of the expected molecular weight (42 KDa for VL-CH2-CH3 and 44 KDa for VH-CH2-CH3 under reducing conditions) could be observed in the cell supernatant. A parallel analysis with non-reducing conditions indicated an apparent molecular weight compatible with the formation of both homodimers and heterodimers.

EXAMPLE 3: DETECTION OF MONO28FC BINDING ACTIVITY BY ELISA

Recombinant human CD28 (R&D Systems, Abingdon, United Kingdom) was used at 1 µg/mL in borate buffer (pH 9.0) to coat 96-well microtiter plates (Immulon, Chantilly, Va.) overnight at 4° C. These immobilized CD28 target molecules will bind only immunoreactive molecules with anti-CD28 activity.

Reactive sites were blocked with 5% skimmed milk in PBS for 2 hours at 37° C. and supernatants from control cells transfected with the plasmid coding for GFP, from cells transfected with only one of the plasmids pSec-VH-Fc(CH2-CH3) or pSec-VL-Fc(CH2-CH3), and from cells co-transfected with pSec-VH-Fc(CH2-CH3) and pSec-VL-Fc(CH2-CH3) were added at different dilutions and reacted for 2 hours at 37° C. Bound Fc fusion proteins with anti-28 activity were revealed with successive incubations (1 hour, 37° C.) with rabbit anti-CD28.3VH/VL (1:2000 dilution; custom preparation at Agrobio, Orleans, France) and horse-radish peroxidase (HRP)—conjugated donkey antirabbit Ig antibodies (1:500 dilution; Jackson ImmunoResearch Laboratories, Bar Harbor, Me.). Bound antibody was revealed by colorimetry using the TMB substrate (Sigma, L'Isle d'Abeau Chesnes, France) read at 450 nm.

The results are shown on FIG. 3 A.

Supernatants from control cells (transfected with the plasmid coding for GFP) or from cells transfected with only one of the plasmids pSec-VH-Fc(CH2-CH3) or pSec-VL-Fc(CH2-CH3) did not contain any detectable level of immunoreactive molecule. This indicated that VH-Fc or VL-Fc homodimers cannot bind CD28. In contrast, supernatants from cells co-transfected with pSec-VH-Fc(CH2-CH3) and pSec-VL-Fc(CH2-CH3) contained dilution-dependant levels of immunoreactive molecules.

Mono28Fc was purified from culture supernatants of COS cells co-transfected with pSec-VH-Fc(CH2-CH3) and pSec-VL-Fc(CH2-CH3) and maintained for 3 days at 37° C.

Supernatants were passed through G-Protein Sepharose columns (Amersham) at a rate of 1 ml/min. The columns were rinsed with PBS and proteins were eluted with glycine buffer (pH 2.8), concentrated by osmotic water retrieval using polyethylene glycol (Fluka, Riedel-de Haen, Germany) and dialysed extensively against PBS at 4° C.

After purification, the Mono28Fc molecules were tested by ELISA as described above. The results are shown on FIG. 3B.

These results show that 50% of the binding activity to CD28 could be reached at a concentration of 100 ng/ml, which represents 1.16 nM.

EXAMPLE 4: DETECTION OF MONO28FC BINDING ACTIVITY BY FLOW CYTOMETRY

The binding of Mono28Fc was confirmed by flow cytometry using CD28+ Jurkat human T cells, which express CD28, or on Raji cells, a human B cell line that does not express CD28.

Jurkat T cells or Raji cells were incubated for 1 hour at 4° C. with purified Mono28Fc proteins or with Fab fragments of CD28.3 (VANHOVE et al., Blood, 102, 564-70, 2003), at 10 µg/ml for 30 min. As a control, cells were incubated with rabbit anti-VII/VH antibodies plus FITC-labeled goat anti-rabbit immunoglobulins only. Bound Fc fusion monomers were detected with a rabbit anti-CD28.3VH/VL and a fluorescein isothiocyanate (FITC)—conjugated donkey anti-rabbit Ig antibody (dilution 1:200; Jackson ImmunoResearch Laboratories) for 30 minutes at 4° C. Cells were then analyzed by fluorescence-activated cell sorting (FACS).

The results are shown on FIG. 4. Both mono28Fc and the Fab fragment of CD28.3 bind Jurkat T cells. In contrast, no binding of the mono28Fc protein could be observed on Raji cells, a human B cell line that does not express CD28. These data demonstrate mono28Fc that binds specifically to $CD28^+$ cells.

EXAMPLE 5: MONO28FC HAS NO AGONIST ACTIVITY ON HUMAN T CELLS

To verify that mono28Fc binds to CD28 and does not induce activation of the target T cell, we compared the biological effect of Mono28Fc with those of the superagonistic antibody ANC28.1 (WAIBLER et al., PLoS ONE, 3, e1708, 2008), or of sc28AT, a monovalent anti-CD28 ligand without Fc domain (VANHOVE et al., Blood, 102, 564-70, 2003).

Human PBMC ($10^5$/well) were cultivated in culture medium without additive (control), or in culture medium with 10 µg/ml of mono28Fc, of sc28AT, or of ANC28.1 for 3 days. 0.5 µCi $^3$H-tymidine was added for the last 16 h of the culture. Incorporated radioactivity was evaluated on a scintillation counter after transfer on nitrocellulose membranes. The results are shown on FIG. 5.

As expected, ANC28.1 induced a robust proliferation of the target cells. In contrast, Mono28Fc, as well as sc28AT did not induce any response in this assay.

EXAMPLE 6: PHARMACOKINETICS OF MONO28FC IN MICE

Recombinant proteins fused with an Fc fragment and immunoglobulins usually present an extended half-life in vivo because they are recognised by the FcRn receptor presented on endothelial and epithelial cells allowing the recycling of that molecules back in the circulation. To determine if our Mono28FC molecule also presents an extended half-live, we followed the distribution in mice of Mono28Fc in comparison with monovalent Fab 28.3 antibody fragments and native IgG CD28.3 antibodies.

Each protein tested (288 µg per injection) was injected into the tail vein of male Swiss mice. Blood samples (2 µL) were collected at different times from the tail vein. The proteins were quantified by measuring the CD28 binding activity in blood samples by ELISA. The data were analyzed by Siphar software (Simed, Utrecht, The Netherlands) with the use of a 2-compartment model. Significance was evaluated with an non-parametric ANOVA test followed by a Bonferroni's Multiple Comparison Test.

The results are shown on FIG. 6.

The distribution half-live ($T_{1/2}\alpha$) was of 2.5±1.1; 5.1±0.3 and 5.4±1.2 hours for IgG, Fab and Mono28Fc, respectively. The elimination half-live ($T_{1/2}\beta$) was of 119±19; 39±6 and 83±26 hours for IgG, Fab and Mono28Fc, respectively (FIG. 6). The data reveal a significant increase of the elimination half-life of Mono28Fc, as compared with Fab fragments, whereas no statistical difference is pointed out when Mono28Fc is compared with a divalent IgG.

EXAMPLE 7: COMPARISON OF MONO28FC WITH A CONSTRUCTION COMPRISING THE CH1-CH2-CH3 IG HEAVY CHAIN DOMAINS

The human IgG1 CH1-CH2-CH3 cDNA was given by Dr. S. Birkle (Univ. Nantes, France). It was inserted into the pcDNA3.1 into the HindIII/BamHI restriction sites, resulting in the pcDNA3.1-CH1-CH2-CH3 plasmid. VH and VL domains corresponding to the CD28.3 antibody anti-human CD28 (NUNES et al., Int Immunol, 5, 311-5, 1993) were amplified as described in Example 1 above, digested with the NheI enzyme and inserted separately into the NheI site of the pcDNA3.1-CH1-CH2-CH3 plasmid. The VH-CH1-CH2-CH3 and VL-CH1-CH2-CH3 cassettes were then excised by EcoRV/XbaI digestion and inserted into the EcoR V digested pSecTag2B vector (Invitrogen), as disclosed in Example 1.

After transfection in Cos cells, messenger RNA molecules corresponding to the two chains were equally synthesised (FIG. 7A). The analysis of proteins by western blotting revealed the synthesis of some corresponding molecules, although clearly more abundant within the cell (FIG. 7B, left panel) than in the supernatant (FIG. 7B, right panel) for the light chain (VL-CH1-CH2-CH3). By immunohistology, the synthesis of both heavy and light chains by transfected Cos cells could be confirmed (FIG. 7C). By ELISA, no CD28 binding activity could be detected in the supernatant (data not shown) nor in transfected cell lysates (FIG. 7D).

The invention claimed is:

1. A recombinant antibody derived from a parent antibody directed against an antigen of interest, wherein said recombinant antibody is an heterodimer of:
   i. a first protein chain consisting essentially of, from its N-terminus to its C-terminus:
      a. a region A having the structure of the variable domain of the heavy chain of an immunoglobulin, said region A comprising the CDRs of the heavy chain of said parent antibody;
      b. a region B consisting of a peptide linker and the CH2 and CH3 domains of an IgG immunoglobulin, wherein said peptide linker comprises one or more cysteine residues;
   ii. a second protein chain consisting essentially of, from its N-terminus to its C-terminus:
      a. a region A' having the structure of the variable domain of the light chain of an immunoglobulin, said region A' comprising the CDRs of the light chain of said parent antibody;
      b. a region B identical to the region B of the first polypeptide;

wherein said first and second protein chains are devoid of a hinge region or any portion thereof and of a CH1 domain of an IgG immunoglobulin, and the first and second protein chains are linked by at least one inter-chain disulfide bond.

2. A recombinant monovalent antibody of claim 1, wherein the peptide linker is a peptide sequence of 1 to 16 amino acids.

3. A recombinant antibody of claim 1, wherein the CH2 and CH3 domains are those of an immunoglobulin of the IgG1 subclass, or of the IgG4 subclass.

4. A recombinant monovalent antibody of claim 1, wherein the region A consists of the variable domain of the heavy chain of the parent antibody.

5. A recombinant monovalent antibody of claim 1, wherein the region A' consists of the variable domain of the light chain of the parent antibody.

6. A recombinant monovalent antibody of claim 1, wherein the parent antibody is the monoclonal immunoglobulin CD28.3, produced by the hybridoma deposited at Collection Nationale de Cultures de Microorganismes under Accession No. CNCM I-2582.

7. A polynucleotide selected from the group consisting of:
(a) a polynucleotide comprising a sequence encoding the first protein chain of a recombinant monovalent antibody according to claim 1; and
(b) a polynucleotide comprising a sequence encoding the second protein chain of a recombinant monovalent antibody according to claim 1.

8. An expression vector comprising a polynucleotide of claim 7.

9. A cell transformed with a polynucleotide (a) and a polynucleotide (b) of claim 7.

10. A method for preparing a recombinant monovalent antibody, wherein said method comprises culturing the transformed cell of claim 9, and recovering said recombinant monovalent antibody from said culture.

11. A medicinal product comprising the recombinant antibody of claim 1.

* * * * *